United States Patent [19]
Steiner et al.

[11] Patent Number: 5,197,490
[45] Date of Patent: Mar. 30, 1993

[54] INFORMATION PROCESSING SYSTEM FOR COUNTING COUGHS OR EVALUATING OTHER ACTIVITIES OF A PATIENT

[75] Inventors: Solomon S. Steiner, Mt. Kisco; Bruce J. Albala, South Salem; Robert Feldstein, Pelham, all of N.Y.

[73] Assignee: CTA Bio Services, Inc., Elmsford, N.Y.

[21] Appl. No.: 510,936

[22] Filed: Apr. 19, 1990

[51] Int. Cl.$^5$ .......................................... A61B 5/0205
[52] U.S. Cl. ................................... 128/782; 128/721; 128/671; 128/715; 128/773
[58] Field of Search ............... 128/721, 671, 782, 715, 128/773

[56] References Cited

U.S. PATENT DOCUMENTS

| | | | |
|---|---|---|---|
| 3,325,799 | 6/1967 | Farris | 128/721 |
| 3,631,438 | 12/1971 | Lewin | 340/240 |
| 4,066,072 | 1/1978 | Cummins | 128/903 |
| 4,179,692 | 12/1979 | Vance | 340/573 |
| 4,240,444 | 12/1980 | Virgulton et al. | 128/782 |
| 4,320,766 | 3/1982 | Alihanka et al. | 128/671 |
| 4,413,620 | 11/1983 | Tucker | 128/734 |
| 4,633,237 | 12/1986 | Tucknott et al. | 340/573 |
| 4,657,026 | 4/1987 | Tagg | 128/721 |
| 4,788,533 | 11/1988 | Mequignon | 340/575 |
| 4,807,604 | 2/1989 | Watson et al. | 128/721 |
| 4,813,436 | 3/1989 | Au | 128/779 |
| 4,848,360 | 7/1989 | Palsgard et al. | 128/773 |
| 4,862,144 | 8/1989 | Tao | 340/573 |

OTHER PUBLICATIONS

Sevelius and Colmore, "Objective Assessment of Antitussive Agents in Patients with Chronic Cough," *The Journal of New Drugs*, Jul.-Aug. 1966, pp. 216–223.

Motorola Telecommunications Device Data, pp. 2–62 to 2–79.

Sevelius, Lester, and Colmore, "Objective Evaluation of Antitussive Agents," *Clinical Pharmacology and Therapeutics*, vol. 6, No. 2, pp. 146–151.

Reece, Cherry, Jr., Reece, Hatcher, and Diehl, "Tape Recorder for Evaluation of Coughs in Children," *Amer. J. Dis. Child*, vol. 112, Aug. 1966, pp. 124–128.

Power, Stewart, Connaughton, Brash, Shapiro, Flenley, and Douglas, "Nocturnal Cough in Patients with Chronic Bronchitis and Emphysema," *Am. Rev. Respir. Dis.*, vol. 130, 1984, pp. 999–1001.

Edwards, Lewis, and Stafford, "The Effect of Pholcodine with and Without an Antihistamine on Cough and Expectoration," *Br. F. Dis. Chest*, vol. 71, 1977, pp. 256–252.

(List continued on next page.)

*Primary Examiner*—William E. Kamm
*Assistant Examiner*—Scott M. Getzow
*Attorney, Agent, or Firm*—Amster, Rothstein & Ebenstein

[57] ABSTRACT

A system using audio and visual information to count coughs or evaluate other discrete information, including respiration and heart rate, relating to a patient in a fixed location such as a bed is disclosed. The system provides movement- and sound-based information derived from the patient's activities to a storage device and subsequently to a signal processing apparatus. One embodiment of the invention includes a pressure transducer, a video camera, a directional microphone, and a videocassette recorder (VCR) having two audio channels. Signals obtained from the transducer and microphone are transmitted to the two audio channel inputs of the VCR, while movement of the patient is recorded using the video camera connected to the video channel input of the VCR. Part or all of the information stored using the VCR may be transmitted to signal processing equipment and frequency filtered to determine the presence and number of coughs, and any remaining information (e.g. the video data) may be used to confirm the count. Because various conditions manifest themselves in movements having different frequency characteristics, the present system, as appropriately modified, also can be used to determine the presence of symptoms such as restlessness and thereby evaluate the effectiveness of medicines such as sedatives and hypnotics.

32 Claims, 1 Drawing Sheet

OTHER PUBLICATIONS

Mascia, "Evaluation of Night Coughing in Asthmatic Children," *The Journal of Asthma Research,* vol. 5, No. 3, Mar., 1968, pp. 163–169.

Archer and Simpson, "Night Cough Counts and Diary Card Scores in Asthma," *Archives of Disease in Childhood,* vol. 60, 1985, pp. 473–474.

Woolf and Rosenberg, "Objective Assessment of Cough Suppressants Under Clinical Conditions Using a Tape Recorder System," *Thorax,* vol. 19, 1964, pp. 125–130.

Kuhn, Hendley, Adams, Clark, and Gwaltney, Jr., "Antitussive Effect of Guaifenesin in Young Adults with Natural Colds," *Chest,* Dec. 1982, pp. 713–718.

Dierckx, Leblanc, Decoster, and Criscuolo, "Double-blind Study of Glaucine in Chronic Cough," *International Journal of Clinical Pharmacology, Therapy and Toxicology,* vol. 19, No. 9, 1985, pp. 396–399.

Ruhle, Criscuolo, Dieterich, Kohler, and Riedel, "Objective Evaluation of Dextromethorphan and Glaucine as Antitussive Agents," *Br. JU. Clin. Pharmac.,* vol. 17, 1984, pp. 521–524.

INFORMATION PROCESSING SYSTEM FOR COUNTING COUGHS OR EVALUATING OTHER ACTIVITIES OF A PATIENT

This invention relates to a system using movement- and sound-based information to count coughs or evaluate other discrete activities of a patient.

BACKGROUND OF THE INVENTION

Coughing, or the sudden, forcible expulsion of air at high velocity, is invariably accompanied by sounds having selected frequency characteristics and differing intensities. Patients with persistent nocturnal coughs frequently complain of sleep disruption caused by the cough reflex, as do those capable of hearing the oft-unpleasant sounds associated with the coughs, including parents of acutely or chronically ill children. To both the patient and those in close proximity, therefore, suppression of the patient's cough reflex desirable. This desirability has led to experimentation with a wide variety of substances as antitussive agents, with the experimentation itself causing a parallel effort to develop methods for accurately and uniformly determining the effectiveness of these medications.

Early attempts at artificially inducing coughing with chemical irritants or using subjective responses in ascertaining effectiveness have been largely unproductive and widely criticized. Artificially inducing coughs leads to increasingly inaccurate measurements as patients develop tolerances to the irritants, while varying the frequency and intensity of the coughs as a function of the concentration of the irritant and the interval between exposures. Although subjective responses may provide valuable evidence of patients, beliefs as to effectiveness, they lack readily quantifiable information useful for comparing the wide range of competing antitussives. In addition, controlled studies have shown the potentially grossly misleading nature of purely subjective responses.

More recent attempts at objectively determining the usefulness of antitussives have included tape recorders as means for capturing sound information concerning coughs emitted by patients. As discussed in Sevelius and Colmore, "Objective Assessment of Antitussive Agents in Patients with Chronic Cough," *The Journal of New Drugs* 216–23 (July–August 1966), sound information related to coughing can be transmitted to a recorder using a throat microphone taped to a patient. Evaluation of the antitussive includes counting the coughs emitted by each patient, a process conducted by manually reviewing the tape recording for each patient. According to Sevelius and Colmore, although intrusive, the throat microphone and attached wiring does not prevent patients from watching television or moving relatively freely throughout a room. Such an intrusive system is, however, likely to disrupt normal sleeping patterns, decreasing both the comfort levels and movement abilities of patients wearing the throat microphones.

Other devices presently used for monitoring the onset of coughs often include a belt worn about the abdomen of the patient and sensors maintained in contact with the body. Typical of these devices are those described in U.S. Pat. Nos. 4,413,620 and 4,240,444 to Tucker and Virgulto, et al., respectively. The patent to Tucker, for example, discloses an abdominal restraint system having a belt designed to inflate in response to signals associated with the onset of coughs. Pressure sensors inserted into the patient using catheters or mounted within the belt are used to detect internal body motion associated with coughing. The apparatus disclosed in Virgulto, et al. similarly includes a belt attached to the patient's body and uses a protruding, displaceable disc to contact a sealed bulb and change its pressure relative to the atmosphere.

Although both the Tucker and Virgulto, et al. devices respond to the onset of coughing, neither apparatus is designed to evaluate the effectiveness of cough-resisting medications by counting the number of coughs emitted. As with the system of Sevelius and Colmore, the intrusiveness of these devices additionally limits their use as evaluation tools in nocturnal environments. Discomfort felt by patients while wearing the devices is likely to inhibit normal sleeping patterns, thereby decreasing the accuracy of any measurements sought to be made.

U.S. Pat. No. 4,848,360 to Palsgard, et al., discloses a less intrusive system used to prevent snoring. According to the Palsgard, et al. patent, a microphone placed beneath the patient's mattress may be used to pass sound information to a series of high- and band-pass filters. The filtered signals subsequently are sent to circuitry designed to measure their periodicity and determine whether the periods correspond to typical time intervals for snore-associated sounds. Once snoring is detected logical signals are transmitted to a counter which activates a vibrational device or other anti-snoring apparatus following receipt of a preselected number of signals.

Like the devices disclosed in the Tucker and Virgulto, et al. patents, the system of Palsgard, et al. is not designed as an evaluation tool for the counting of coughs. The Palsgard, et al. system also lacks storage means beyond the digital counter used to determine if continuous snoring is occurring, preventing any off-line evaluation or visual confirmation of the sleeper's activities. Because some snoring may not alter respiration sufficiently to result in determinable movement by the patient, the system disclosed in Palsgard, et al. similarly lacks any motion detecting means.

SUMMARY OF THE INVENTION

The cough-counting system of the present invention includes means for providing both movement- and sound-based information obtained from a patient to an analog (or digital) storage device such as a videocassette recorder (VCR). The unintrusiveness of the system, which includes a sensor placed beneath the patient or the patient $\propto$ s mattress, avoids interfering with normal sleeping or waking activities. At the same time, however, audio and visual data derived from both the movements and sounds of the patient increase the accuracy of the cough count and provide means for confirming the count if desired. Storing the data also allows processing to be conducted at any convenient time, further reducing the likelihood of disturbing the patient's sleep.

One embodiment of the present invention includes a pressure transducer, video camera, directional microphone, and VCR having two audio channels. Movement of the patient alters the pressure of an unintrusive, partially inflated air mattress relative to atmospheric pressure, varying the voltage emitted by the associated transducer. The transducer signal then is encoded using modified delta-modulation techniques and signals obtained from the encoder and microphone are transmitted to the two audio channel inputs of the VCR. An infrared light source provides illumination unseen by the patient, allowing the patient's movement to be recorded using the video camera (which may be equipped with an auto diaphragm to extend its dynamic range) connected to the video channel input of the VCR. Part or all of the information stored using the VCR may be fed to signal processing equipment, and the audio track may be frequency filtered to determine the presence and number of coughs. Because the encoded information derived from the transducer frequently is sufficient to generate an accurate cough count, the other audio and video data may be used as confirmation if desired. Additional verification information may be obtained using passive techniques designed to record variations in the patient's infrared energy emissions.

The present system also is capable of developing information relating to respiration and heart rate, functioning as a ballistocardiograph, and determining the presence of symptoms such as restlessness, sleep apnea, cardiac arrythmia and, in some cases, bed wetting. Each of these conditions manifests itself in differing patient sound, movement, and infrared emission characteristics, allowing the present system to determine its existence through appropriate processing of information such as that available at the audio and visual inputs of the VCR. By examining these conditions the invention may be used to determine the effectiveness of medicines such as sedatives and hypnotics.

It is therefore an object of the present invention to provide a system for counting the number of coughs emitted by a sleeping patient.

It is another object of the present invention to provide a system for evaluating the effectiveness of cough-resisting medications by counting the number of coughs emitted by a medicated patient.

It is an additional object of the present invention to provide an unintrusive system for detecting both sounds emitted by and movement associated with a patient.

It is a further object of the present invention to provide a system using audio and visual information to evaluate the activities of a patient.

It is yet another object of the present invention to provide a system for recording movement- and sound-based audio and visual information for off-line evaluation of the information relating to coughs, heart rate, respiration, cardiodynamics, or other activities of a patient.

Other objects, features, and advantages of the present invention will become apparent with reference to the remainder of the written portion and the drawings of this application.

DETAILED DESCRIPTION OF THE DRAWING

Figure 1:
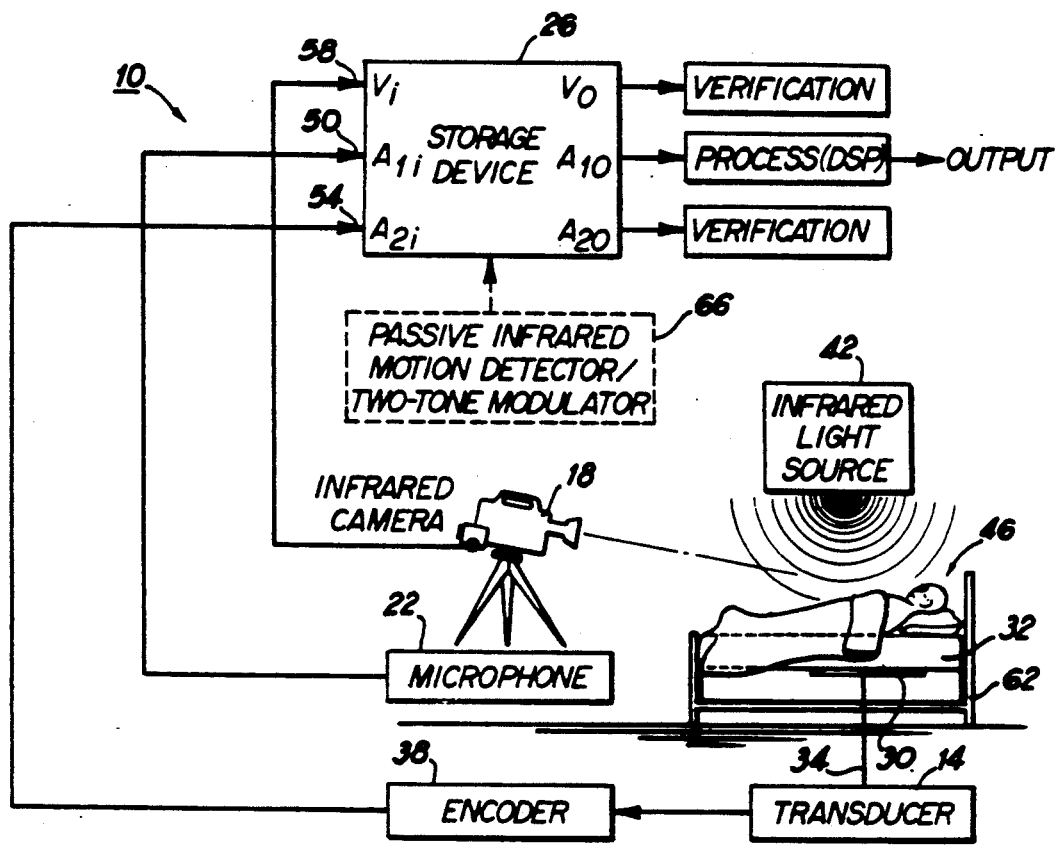
FIG. 1 is a partially schematic representation of the system of the present invention used to evaluate the activities of a sleeping patient.

FIG. 1 details the cough-counting system 10 of the present invention. System 10 includes a pressure transducer 14, video camera 18, microphone 22, and storage device 26 such as a VCR, digital worm drive, optical recorder, or other appropriate storage means. Also shown in FIG. 1 are sensor 30, placed beneath a conventional mattress 32 and connected to transducer 14 by connector 34, encoder 38, and infrared light source 42. System 10 is designed to count the number of coughs emitted by a sleeping or waking patient 46, typically a young child but including an adult or an animal, during a preselected interval. By allowing evaluation of both movement- and sound-based data derived from patient 46, system 10 provides an accurate and easily verifiable determination of the amount of coughing which has occurred.

In one embodiment of the present invention, system 10 includes as storage device 26 a VCR having two audio input channels 50 and 54 and a video input 58. Signals derived from a gauge- or piezoelectric-type transducer 14 and a directional microphone 22 are provided to audio inputs 50 and 54 respectively, while information obtained from video camera 18, which may include an auto-diaphragm or -iris to extend its dynamic range, is directed to video input 58. Magnetic tape within the VCR may be used to record the data for subsequent evaluation, allowing off-line processing to be performed at a remote facility. As a result, system 10 may be conveniently used inside the patient's home, reducing difficulties associated with monitoring patient 46 in a foreign environment.

Before patient 46 retires to bed 62, sensor 30, illustrated in FIG. 1 as an air mattress approximately 24" × 36" × 3" in dimension when fully inflated, is placed beneath conventional mattress 32 (or, if desired, beneath patient 46) and inflated to a depth of approximately 1". Partially inflating sensor 30 maintains the air mattress at approximately atmospheric pressure while minimizing the variation in mattress 32 firmness experienced by patient 46. At the same time, however, sensor 30 remains sensitive to pressure changes caused by, for example, the coughing, respiration, or heart rate of patient 46. Once patient 46 enters bed 62 a baseline pressure may be established at transducer 14 from which deviations may be determined. The patient's surroundings also may be illuminated by infrared light source 42, allowing infrared recording video camera 18 to function in either the absence or presence of visible light.

Evidence of coughing emitted from patient 46 may be recorded in a variety of ways. As the diaphragm of patient 46 moves in response to a cough, pressure deviations at sensor 30 are transmitted to transducer 14. Hollow plastic tubing may be used as connector 34 to transmit air pressure information to transducer 14, although those having ordinary skill in the art will recognize that sensor 30 itself may be a pressure transducer or any other device suitable for measuring movement of patient 46. Transducer 14, in one embodiment having a range of 0–1.5 psi and capable of withstanding 15 psi without calibration shift, converts the differential pressures (relative to atmospheric pressure) into electrical signals for storage on the magnetic tape contained within the VCR or other appropriate storage means used as storage device 26. Because the output of transducer 14 usually falls within a relatively narrow range of values and contains accuracy-reducing noise components, the signal may be passed through a low pass filter (not shown) before being encoded for recording.

Microphone 22 and video camera 18 similarly may record the presence of coughing, with the microphone 22 receiving sound waves emitted by patient 46 and the video camera 18 recording the muscular spasms associated with coughs. Signals from microphone 22 are transmitted to audio input 54 of storage device 26, while the signals from video camera 18 are forwarded to video input 58. A passive infrared system 66, designed to detect variations in the infrared energy emissions of patient 46, may be used to determine the presence of coughing as well.

Figure 2:
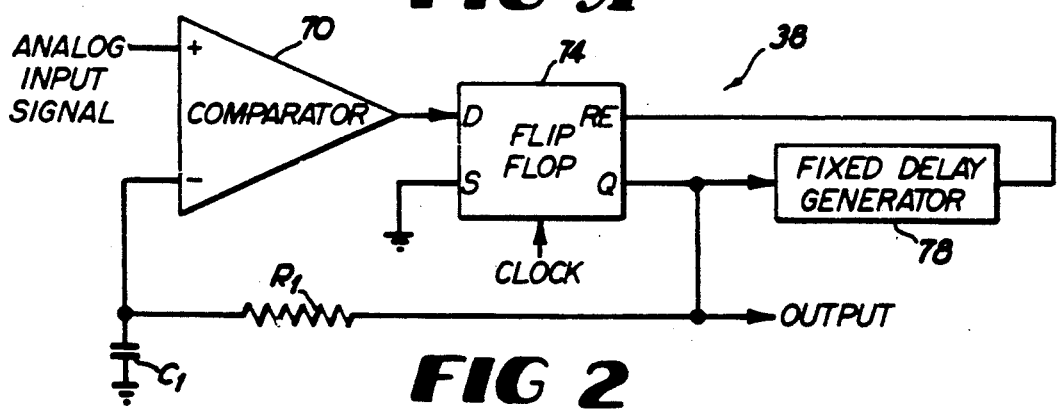
FIG. 2 is a schematic representation of an electronic circuit used to encode analog signals obtained in connection with the system of FIG. 1 for subsequent processing.

Encoder 38 (FIG. 2), designed to encode the analog signal from transducer 14 in serial form, includes a comparator 70, flip-flop 74, fixed delay r 78, resistor ("$R_1$"), and capacitor ("$C_1$"). An analog signal, which may be the output of transducer 14 and in some embodiments has a bandwidth of 0–2.5 Hz, is transmitted to the positive terminal ("+") of comparator 70. The output of comparator 70 then is strobed into the input ("D") of flip-flop 74 with each clock pulse ("CLOCK"), and the output value ("Q") of flip-flop 74 is sent through fixed delay generator 78 back to the reset terminal ("RE") of flip-flop 74. The output value ("Q") of flip-flop 74 also serves as the output of encoder 38, and is fed back to the negative terminal ("−") of comparator 70 through resistor ("$R_1$") and capacitor ("$C_1$"). As illustrated in FIG. 2, the set terminal ("S") of flip-flop 74 is grounded. In addition, choosing 5 kHz for the "CLOCK" frequency and 10 Hz for $R_1C_1$ (i.e. The product of "$R_1$" multiplied by "$C_1$") makes pulse recovery relatively easy during processing and reduces tracking error substantially.

Encoder 38 performs a modified form of delta modulation. Traditional delta modulation includes comparison of an input signal to the average value of the system output, with the result of the comparison being clocked into a flip-flop. The output of the flip-flop also serves as the system output, which is averaged using an RC circuit and transmitted back to the positive terminal of the comparator. The system output consists of a square wave having transitions synchronous with the clock pulses, with the input information encoded in the transitions which do and do not occur. Although traditional delta modulation serves as a useful technique for encoding analog signals in serial form, its large bandwidth requirements, resolution limitations, and inability to compensate for output data recovery drift diminish its effectiveness in connection with system 10 of the present invention. By modifying traditional circuitry to, among other things, include fixed delay generator 78, however, encoder 38 may compensate for such output drift and allow the output ("Q") of flip-flop 74 to maintain fidelity for all values from D.C. to 2.5 Hz at the comparator 70 input.

Figure 3:
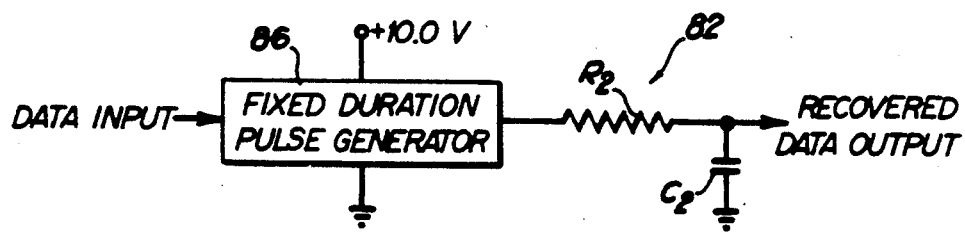
FIG. 3 is a schematic representation of an electronic circuit used to decode the signals encoded using the circuit of FIG. 2.

An important feature of encoder 38 is that it allows processing to begin at any point in the data stream, as the recovered information will converge to the correct input values with a tim e constant of $10R_1C_1$. FIG. 3 details a circuit 82 for recovering the input data, which includes fixed duration pulse generator 86 and a resistor ("$R_2$") and capacitor ("$C_2$") network. The output of circuit 82 then may be appropriately processed to determine the quantity of coughs emitted (or other quantifiable behavior performed) by patient 46 during a specified interval.

The foregoing is provided for purposes of illustration, explanation, and description of embodiments of the present invention. Modifications and adaptations to these embodiments will be apparent to those of ordinary skill in the art and may be made without departing from the scope or spirit of the invention. In particular, system 10 may be used to detect and evaluate information relating to respiration, heart rate, and various other types of motion and activities of patient 46, and may function as a ballistocardiogram. Moreover, sensor 30 may comprise a variety of multi-chambered air mattresses, depending on the type of patient 46 behavior desired to be measured. Single chambered mattresses allow air to move freely within the total volume enclosed, permitting transducer 14 to provide an accurate reflection of deviations in the total load on sensor 30. If measurements of more localized activity, such as various types of patient motion (including, for example, propping on an elbow) are desired, however, the single-chambered air mattress could be replaced with one having a number of seams extending much of the length or width of the mattress, thereby dividing it into narrow channels. The seams would prevent rapid equilibrium within the mattress and allow local transient pressure to be sensed at the output pressure port. Similarly, if localized data sensitivity is desired in addition to overall load pressure, the multichambered mattress could be designed to include seams extending virtually its entire width or length (but not completely sealing any channel from the others), with pressure ports placed in each channel, and separate transducers employed to allow outputs to consist of individual measurements or "summary" recordings based on, for example, weighted sum and difference measurements.

We claim:

1. A system for counting coughs emitted by a patient recumbent upon a mattress, comprising:
    a. an air mattress positionable beneath the mattress for sensing pressure changes caused by the emitted coughs;
    b. a pressure transducer connectable to the air mattress for converting the pressure changes to a first series of electrical signals;
    a microphone remote from the patient for sensing sounds caused by the emitted coughs and converting the sounds to a second series of electrical signals; and
    d. a recorder having first and second inputs for receiving the first and second series of electrical signals, respectively.

2. A system according to claim 1 further comprising:
    a. hollow tubing for connecting the air mattress to the pressure transducer;
    b. an infrared video camera having an auto diaphragm and associated light source for sensing video information related to the patient's movement; and
    c. a third input to the recorder for receiving the sensed video information.

3. A system according to claim 2 further comprising:
    a. an encoder interposable between the pressure transducer and recorder for encoding the first series of electrical signals;
    b. means for decoding the encoded first series of electrical signals; and
    c. means for signal processing at least one series of signals selected from the group comprising:
        i. The first series of electrical signals;

ii. The second series of electrical signals;
iii. The encoded first series of electrical signals; and
iv. The decoded first series of electrical signals.

4. A system according to claim 1 further comprising:
   a. an encoder interposable between the pressure transducer and recorder for encoding the first series of electrical signals;
   b. means for decoding the encoded first series of electrical signals; and
   c. means for signal processing at least one series of signals selected from the group comprising:
      i. The first series of electrical signals;
      ii. The second series of electrical signals;
      iii. The encoded first series of electrical signals; and
      iv. The decoded first series of electrical signals.

5. A system for acquiring desired information regarding a monitored condition of a patient comprising:
   (a) a pressure responsive sensing system activated by the presence of said patient at a monitoring location for producing signals indicative of said presence;
   (b) a sound sensing system for sensing the sounds emitted by the patient to produce signals indicative of the monitored condition; and
   (c) an information acquisition system for receiving and storing the signals form said pressure responsive sensing system and said sound sensing system to permit determination of desired information regarding the monitored condition of said patient when the patient is present at said patient monitoring location.

6. The system according to claim 5 wherein said monitored condition corresponds to the coughing emitted by said patient at the patient monitoring location.

7. The system according to claim 5 wherein said pressure responsive sensing system includes a pressure transducer and a system for transmitting changes in pressure caused by said patient to said transducer, said pressure transducer producing signals indicative of the presence of the patient at the monitoring location and of the monitored condition of the patient.

8. The system according to claim 5 wherein said information acquisition system comprises a video tape recorder.

9. A system for acquiring desired information regarding a monitored condition of a patient comprising:
   (a) a presence sensing system for producing a presence signal indicative of the presence of said patient at a patient monitoring location;
   (b) a monitoring system for producing monitoring signals indicative of the monitored condition of said patient, said monitoring system including a sound sensor for generating audio monitoring signals corresponding to sounds emitted by the patient; and
   (c) an information acquisition system for receiving and storing said presence signal and said audio monitoring signals to permit determination of desired information regarding the monitored condition of the patient when the patient is present at said patient monitoring location.

10. The system according to claim 9 wherein said sounds emitted by the patient are indicative of the respiratory condition of the patient.

11. The system according to claim 9 wherein said sounds emitted by the patient are indicative of the physiological condition of the patient.

12. The system according to claim 9 wherein said presence sensing system includes a pressure responsive sensor responsive to pressure produced by said patient when said patient is at said patient monitoring location for producing said presence signal.

13. The system according to claim 12 wherein said monitoring system senses the monitored condition of said patient by sensing sounds emitted by said patient.

14. The system according to claim 12 wherein said pressure responsive sensor isnot in contact with said patient.

15. The system according to claim 9 wherein said system includes a pressure responsive sensor responsive to variations in pressure caused by the presence of said patient at said monitoring location for producing said presence signal and said monitoring signals indicative of the monitored condition of the patient.

16. The system according to claim 15 wherein said pressure responsive sensor is not in contact with said patient.

17. The system according to claim 15 wherein said pressure sensor includes an inflatable bladder and a pressure transducer connected thereto.

18. The system according to claim 9 wherein said monitored condition is the coughing emitted by the patient.

19. The system according to claim 9 wherein the information acquisition system comprises a video tape recorder.

20. The system according to claim 19, further including a video camera connected to said video tape recorder for video monitoring of the patient.

21. The system according to claim 9 wherein said information acquisition system encodes the signals generated by said monitoring system.

22. A system for acquiring desired information regarding a monitored condition of a patient comprising:
   (a) a presence sensing system including a pressure sensor spaced part from the patient for producing a presence signal indicative of the presence of the patient at a monitored location;
   (b) a sound sensor for generating audio signals corresponding to sounds emitted by the patient; and
   (c) an information acquisition system for receiving said presence and said audio signals to permit determination therefrom of desired information regarding the monitored condition of the patient when the patient is present at said patient monitoring location.

23. The system according to claim 22 wherein said pressure sensing system includes an inflatable bladder and a pressure transducer connected thereto.

24. The system according to claim 22 wherein said monitored condition is the coughing emitted by the patient.

25. The system according to claim 22 wherein said information acquisition system comprises a video tape recorder.

26. The system according to claim 25, further including a video camera connected to said video tape recorder for video monitoring of the patient.

27. A method for acquiring desired information regarding a monitored condition of a patient comprising the steps of:
   (a) producing a first signal indicative of the presence of the patient at a monitoring location;

(b) sensing sounds emitted by the patient which are indicative of the monitored condition and generating corresponding audio signals; and (c) acquiring and storing said first signal and said audio signals to permit determination therefrom of desired information regarding the monitored condition of the patient when the patient is present at said patient monitoring location.

28. The method of claim 27 wherein the step of producing said first signal corresponds to sensing pressure variations induced by the presence of said patient at said monitoring location.

29. The method of claim 27 wherein said sensing of audio signals provides information as to the coughs emitted by the patient.

30. A method of acquiring desired information regarding a monitored condition of a patient comprising the steps of:

(a) measuring a first pressure change at a location that is spaced apart from the patient to generate a signal indicative of the presence of said patient at a monitoring location;

(b) measuring a second pressure change associated with said monitored condition of said patient and generating signals corresponding thereto, said first and second pressure changes being measured by monitoring the changes in pressure in an inflatable bladder having a transducer connected thereto; and (c) acquiring and storing said signals corresponding to said fist and second pressure changes to permit the determination of desired information regarding the monitored condition of said patient.

31. The method of claim 30 wherein the step of measuring said second pressure changes provides signals indicative of coughs emitted by the patient.

32. The method of claim 30 further including the steps of sensing sounds emitted by the patient to produce audio signals further indicative of said monitored condition and acquiring and storing said audio signals along with said signals corresponding to said first and second pressure changes.

* * * * *